US012797768B2

(12) United States Patent
Kleiber et al.

(10) Patent No.: US 12,797,768 B2
(45) Date of Patent: Nov. 17, 2026

(54) METHOD AND DEVICE FOR SEPARATING A HYDROCARBON-CONTAINING FEEDSTOCK STREAM BY EXTRACTIVE DISTILLATION

(71) Applicants: thyssenkrupp Uhde GmbH, Dortmund (DE); thyssenkrupp Uhde Engineering Services GmbH, Bad Soden am Taunus (DE); thyssenkrupp AG, Essen (DE)

(72) Inventors: Michael Kleiber, Hattersheim (DE); Simone Bettinger, Bad Soden/Taunus (DE); Frank Schuch, Dortmund (DE); Martin Gratowski, Frankfurt (DE); Helmut Gehrke, Bergkamen (DE)

(73) Assignees: thyssenkrupp Uhde GmbH, Dortmund (DE); thyssenkrupp Uhde Engineering Services Gmbh, Bad Soden am Taurus (DE); thyssenkrupp AG, Essen (DE)

( * ) Notice: Subject to any disclaimer, the term of this patent is extended or adjusted under 35 U.S.C. 154(b) by 180 days.

(21) Appl. No.: 18/709,396

(22) PCT Filed: Nov. 2, 2022

(86) PCT No.: PCT/EP2022/080503
§ 371 (c)(1),
(2) Date: May 10, 2024

(87) PCT Pub. No.: WO2023/083655
PCT Pub. Date: May 19, 2023

(65) Prior Publication Data
US 2025/0041758 A1 Feb. 6, 2025

(30) Foreign Application Priority Data
Nov. 12, 2021 (BE) .................................. 2021/5880
Nov. 12, 2021 (DE) ..................... 10 2021 212 775.4

(51) Int. Cl.
*B01D 3/40* (2006.01)
*B01D 3/14* (2006.01)
(Continued)

(52) U.S. Cl.
CPC ................. *B01D 3/14* (2013.01); *B01D 3/40* (2013.01); *C07C 7/08* (2013.01); *C10G 21/28* (2013.01); *C10G 2400/30* (2013.01)

(58) Field of Classification Search
CPC .. B01D 3/40; B01D 3/141; C07C 7/08; C07C 7/10; C10G 21/28
See application file for complete search history.

(56) References Cited

U.S. PATENT DOCUMENTS 3,451,925 A 6/1969 Morris et al.
3,476,680 A 11/1969 Coleman
(Continued)

FOREIGN PATENT DOCUMENTS

CA 610414 A 12/1960
CA 1 055 876 6/1979
(Continued)

OTHER PUBLICATIONS

English Translation of International Search Report issued in PCT/EP2022/080503, dated Jan. 31, 2023.
(Continued)

*Primary Examiner* — Jonathan Luke Pilcher
(74) *Attorney, Agent, or Firm* — thyssenkrupp North America, LLC

(57) ABSTRACT

The disclosure relates to a process for separating a hydrocarbon-containing feedstock stream by extractive distillation, wherein the feedstock stream is contacted with a water-soluble solvent for aromatics in countercurrent. An aliphatics fraction is distillatively removed as aliphatics product stream from the mixture obtained. The aromatics are
(Continued)

stripped from the aromatics-enriched solvent that remains and the aromatics-depleted solvent is recycled in a solvent circuit, with compounds having a lower boiling point compared to the solvent accumulating in the solvent circuit as impurities. At least a substream of the solvent circuit is purified for removal of the impurities, wherein the substream for the purifying is subjected to a thermal separation process, in which the impurities are at least partly discharged in a top product and the purified solvent that remains is recycled into the solvent circuit. An apparatus for carrying out the process is also disclosed.

15 Claims, 4 Drawing Sheets

(51) Int. Cl.
*C07C 7/08* (2006.01)
*C10G 21/28* (2006.01)

(56) References Cited

U.S. PATENT DOCUMENTS

| | | | | |
|---|---|---|---|---|
| 4,201,633 | A * | 5/1980 | Paret | C07C 7/08 585/808 |
| 4,997,547 | A | 3/1991 | Emmrich et al. | |
| 8,362,314 | B2 * | 1/2013 | Stabel | C07C 7/08 585/860 |
| 8,378,164 | B2 * | 2/2013 | Stabel | C07C 7/08 585/860 |
| 8,536,397 | B2 | 9/2013 | Noll et al. | |
| 8,680,358 | B1 | 3/2014 | Lee et al. | |
| 9,221,729 | B1 * | 12/2015 | Lee | C10G 21/28 |
| 9,370,728 | B2 | 6/2016 | Cretoiu et al. | |
| 9,822,315 | B2 | 11/2017 | Khandelwal et al. | |
| 2010/0228072 | A1 | 9/2010 | Stabel et al. | |
| 2010/0305382 | A1 | 12/2010 | Stabel et al. | |
| 2012/0037542 | A1 * | 2/2012 | Wu | C10G 21/28 208/313 |
| 2015/0210934 | A1 | 7/2015 | Khandelwal et al. | |
| 2016/0288014 | A1 * | 10/2016 | Garg | C10G 21/28 |
| 2017/0029348 | A1 | 2/2017 | Bender | |
| 2021/0053893 | A1 | 2/2021 | Tian et al. | |

FOREIGN PATENT DOCUMENTS

| | | | |
|---|---|---|---|
| DE | 10 2007 039 074 | A1 | 2/2009 |
| DE | 10 2012 111 292 | A1 | 5/2014 |
| EP | 0 329 958 | A2 | 8/1989 |
| FR | 2259891 | | 8/1975 |
| WO | 99/11740 | A1 | 3/1999 |
| WO | 2010/068614 | A1 | 6/2010 |
| WO | 2013/134082 | A1 | 9/2013 |
| WO | 2014/134077 | A1 | 9/2014 |
| WO | 2015/112928 | A1 | 7/2015 |
| WO | 2019/149212 | A1 | 8/2019 |

OTHER PUBLICATIONS

"World Market Leader in Aromatics Extraction", TKIS Aromatics Brochure (see p. 22-23), 36 pages (2015).

* cited by examiner

METHOD AND DEVICE FOR SEPARATING A HYDROCARBON-CONTAINING FEEDSTOCK STREAM BY EXTRACTIVE DISTILLATION

CROSS REFERENCE TO RELATED APPLICATIONS

This application is a U.S. National Stage Entry of International Patent Application Serial Number PCT/EP2022/080504, filed Nov. 2, 2022, which claims priority to German Patent Application No. DE 10 2021 212 775.4, filed Nov. 12, 2021, and Belgian Patent Application No. BE 2021/5880, filed Nov. 12, 2021, the entire contents of which are incorporated herein by reference.

FIELD

The present disclosure generally relates to a process for separating a hydrocarbon-containing feedstock stream by extractive distillation.

BACKGROUND

Aromatics, in particular the simplest aromatic compounds benzene, toluene and xylene, are of industrial importance as intermediates for the chemical industry. Various industrial processes are known for obtaining aromatics. One type of process which achieves a particularly high purity of the aromatics product stream with comparatively low costs is the obtaining by extractive distillation from a hydrocarbon-containing feedstock stream. Examples of feedstock streams that may be considered include naphtha, pyrolysis gasoline, reformate gasoline or also coking plant light oil. Heavy components are preferably removed from the feedstock stream prior to recovery of the aromatics, for example by removal of the $C_{8+}$ fraction.

When recovering aromatics by extractive distillation, the feedstock stream is contacted in countercurrent with a selective solvent for aromatics. The solvent influences the volatility of the various constituents of the feedstock stream to varying degrees. The volatility of the aromatic constituents is reduced by the dilution, while that of the aliphatic constituents is markedly increased. In this way, a distillative separation into aromatics and nonaromatics/aliphatics is made possible. In a first step, the aromatics dissolved in the solvent are then separated according to a thermal separation cut by means of extractive distillation from the aliphatic constituents of the feed mixture, which are discharged as top product of the distillation. In a second step, the aromatics are driven out from the solvent as top product by stripping. The aromatics product stream can then be separated further into individual aromatics fractions. The aromatics-depleted solvent is recycled into the extractive distillation and reused. In this way, individual aromatics can be obtained in pure form in a continuous process.

Solvents known for the extractive distillation include, inter alia, sulfolane, methylsulfolanes, N-methylpyrrolidone, N-formylmorpholine, ethylene glycol and mixtures thereof, and also mixtures of the mentioned solvents with water. The solvents or solvent mixtures used are water-soluble.

The sustained reuse of the same solvent in a solvent circuit results in the accumulation in the solvent of impurities, which neither leave the process as top product of the distillative removal of the aliphatics nor as top product in the stripping of the aromatics. As a result of operator efforts to optimize the energy efficiency of the plants and to save operating materials, such impurities arise to an increasing extent also in the feedstock stream of plants serving solely to recover benzene and toluene. Especially in plants that are used not just for the recovery of benzene and toluene but also at the same time for the recovery of xylene, the accumulation of such impurities can hardly be avoided over the long term, since the feedstock stream in this case must contain a relatively large proportion of higher-boiling components. In addition, processes connected upstream of the extractive distillation, such as for example clay treatment, can introduce heavy components that accumulate in the solvent. However, it is also possible that, as a result of incorrect operation or malfunctions of plant parts connected upstream of the extractive distillation, these parts for example serving to remove higher-boiling fractions, there is increased contamination of the solvent circulating in the extractive distillation with high-boiling impurities.

Over the course of time, the impurities lead to the solvent losing its extractant power and needing to be replaced. In order to reduce the costs associated with replacing the solvent, it is desirable to have the option of purifying the solvent in the solvent circuit, by means of which the impurities are removed. In this way, the cycle time until replacement of the solvent can be considerably extended.

For purification of the solvent, it is known for example from US 2010/0228072 A1 to subject a substream of the solvent circuit to a distillation, with the purified solvent leaving the distillation as top product and impurities remaining behind as distillation residue being removed from the plant. The disadvantage with this type of purification is that only impurities that are higher boiling compared to the solvent can be removed from the solvent circuit. Impurities that are lower boiling than the solvent or are co-boilers with the solvent, that is to say which have a very similar boiling point, remain in the solvent.

It is thus known from DE 10 2012 111 292 A1 to add water to a substream of the extractant withdrawn from the bottom of the stripper column and supply this substream to a distillation column. In the distillation column, the extractant is separated from the added water and from hydrocarbons dissolved in the extractant. Water and hydrocarbons are discharged via the top of the distillation column. This type of purification is based on the extractant dissolving in the water and the water-insoluble hydrocarbons thus being displaced from solution in the extractant and forming a more volatile phase that can be removed with the water by distillation. However, the disadvantage is that a large amount of water needs to be used in order to treat the entire extractant. The entire amount of water used, at least in the case of an extractive distillation with largely anhydrous solvent, must then be distilled off again. The known process for purifying the solvent is thus associated with high energy expenditure and costs.

Thus a need exists to specify a process and an apparatus for separating a hydrocarbon-containing feedstock stream by extractive distillation, in which the selectivity and capacity of the solvent used is ensured over a long period by means of a resource-efficient process.

BRIEF DESCRIPTION OF THE FIGURES

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION

Figure 1:
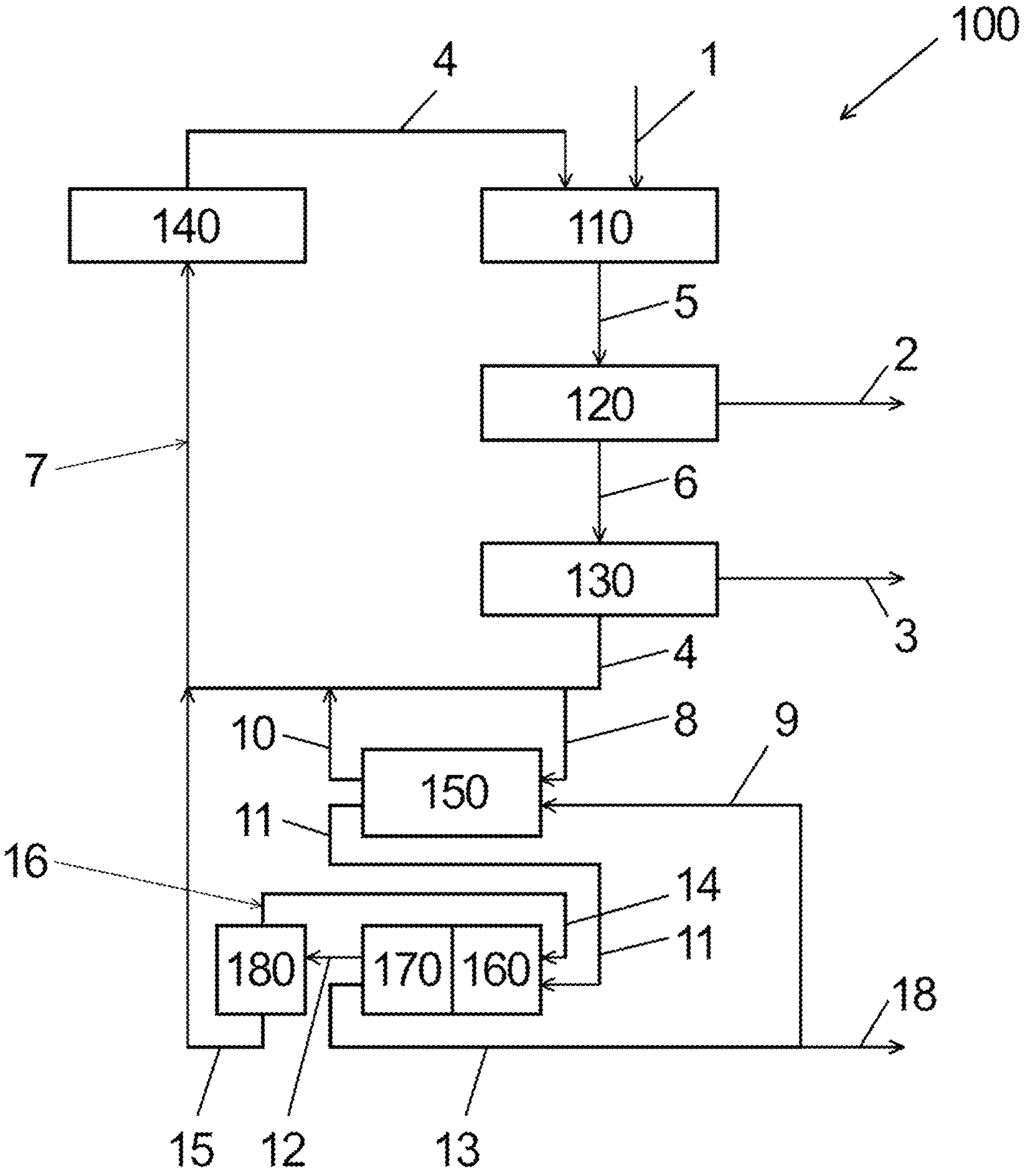
FIG. 1 schematically shows a flow diagram of the process according to the invention according to a first exemplary embodiment in which a substream of the solvent circuit is purified by a thermal separation process.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

A process for separating a hydrocarbon-containing feedstock stream by extractive distillation into at least one aliphatics product stream and one aromatics product stream is provided thereby, comprising the following steps:

- contacting the feedstock stream with a water-soluble solvent for aromatics in countercurrent,
- distillatively removing an aliphatics fraction from the mixture obtained to leave behind the aromatics-enriched solvent and discharging the aliphatics fraction in the aliphatics product stream,
- stripping the aromatics from the aromatics-enriched solvent and discharging the aromatics in the aromatics product stream,
- recycling the aromatics-depleted solvent in a solvent circuit for the extraction of further aromatics from the feedstock stream, with compounds having a lower boiling point compared to the solvent accumulating in the solvent circuit as impurities, and
- purifying at least a substream of the aromatics-depleted solvent for removal of the impurities.

According to the invention, it is provided that the substream for the purifying is subjected to a thermal separation process, in which the impurities are at least partly discharged in a top product and the purified solvent that remains is recycled into the solvent circuit.

For the purposes of the invention, the substream can comprise any desired proportion of the overall solvent circuit. In particular, the substream can also be the entire solvent stream in the solvent circuit. Preference is given to a substream in the purification that corresponds to a proportion of 1% by mass to 20% by mass of the overall solvent stream in the solvent circuit.

As a result of the thermal separation process, the impurities that are more volatile compared to the solvent are removed from the solvent and discharged as a separate top product.

The separation cut of the thermal separation process is preferably selected so that the purified solvent obtained as bottom product contains not more than 5% by mass, particularly preferably not more than 1% by mass, of low-boiling impurities. In order to achieve a purity of the purified solvent that is sufficient in this sense, co-boilers with the solvent and a portion of the solvent itself are preferably also discharged in the top product in the thermal separation process.

For the purposes of the present disclosure, a component can be considered to be low boiling in relation to the solvent when its boiling point (at the operating pressure of the thermal separation process) is at least 10 K lower than the boiling point of the solvent, or when the component forms with the solvent an azeotrope that is low boiling in this sense. Components or azeotropes having a boiling point in the range +/−10 K about the boiling point of the solvent are considered to be co-boilers with the solvent. For the purposes of the present disclosure, the boiling point of a substance without further specification of the ambient conditions is to be understood to be the normal boiling point of the substance. If a mixture of two or more components is being used as solvent, the term "boiling point of the solvent" for the purposes of the present disclosure refers to the boiling point of the lowest-boiling component of the solvent mixture.

The application of a thermal separation process to the substream of the solvent circuit has the advantage that it does not require the addition of an additional extractant-such as for example water or an extractant for aliphatics—to the substream, which would then in turn have to be removed from the solvent. According to the invention, therefore, no additives need to be introduced into the solvent circuit for the actual purification of the solvent. This is particularly advantageous in processes for the direct, water-free production of aromatics, in which the water content in the solvent circuit has to be kept sufficiently low. By dispensing with an additional extractant, the process according to the invention can also be integrated as a retrofit solution particularly simply into existing plants for the extractive distillation of aromatics.

In preferred embodiments, a recovery of solvent from the top product is carried out additionally to the purification of the solvent. For this, the following further steps are provided:

- adding water to the top product to form an aqueous solvent-containing phase and a hydrophobic phase,
- separating the aqueous phase from the hydrophobic phase and
- distilling the aqueous phase for the removal of water by distillation, with the bottom product of the distillation being recycled into the solvent circuit.

The recovery of the solvent from the top product leads to a lower solvent consumption and facilitates the further processing/disposal of the top product. The recovery of the solvent from the top product thus constitutes a particularly cost-efficient and environmentally friendly variant of the process according to the invention.

If for the recovery of the solvent water is added only to the top product of the thermal separation process and not to the entire substream to be purified of the solvent circuit, the amount of water to be used is markedly reduced, since the top product has a solvent content that is lower by orders of magnitude. The energy requirement for the distillation of the aqueous phase is thus substantially reduced compared to the known processes for solvent purification that are based solely on washing with water. Preference is given to adding water to the top product in a ratio by mass in the range from 10:1 to 1:1.

Preferably, the water removed by distillation is recycled in a water circuit and again added to the top product of the thermal separation process. The reuse of the water in a water circuit reduces the amount of waste waters requiring treatment produced and ensures resource-efficient operation.

It is further preferable that the substream is cooled in a heat exchanger prior to carrying out the thermal separation process and the distillation is carried out using the heat energy obtained in the heat exchanger. A temperature of the substream in the range from 140° C. to 200° C. is advantageous for carrying out the thermal separation process. The thermal separation at a lower temperature compared to the temperature of the stripping (approx. 160° C.-240° C.) reduces the thermal stress on the solvent and at the same time makes it possible to utilize the heat energy in the solvent recovery. The amount of energy obtained when cooling the substream in the heat exchanger is generally more than enough for carrying out the distillation. Alternatively or in addition, heat energy from the main stream of the solvent circuit can be extracted for operating the distillation column.

Preferably, the distillation is carried out with a top pressure of less than 1 bar (a), especially preferably less than 500 mbar (a) and particularly preferably less than 200 mbar (a). When carrying out the distillation in a vacuum, the boiling point of the water is lowered and thus the temperature in the distillation bottoms is reduced. This makes it possible to reduce the amount of energy required for the distillation and avoids undesirable side reactions in the distillation bottoms. The vacuum is preferably set such that the bottom temperature is in a range up to at most 230° C., particularly preferably between 150° C. and 200° C.

After water has been added to the top product and the aqueous phase has been separated, a hydrophobic phase is present predominantly containing the impurities to be discharged. In preferred embodiments of the process it is provided that a substream of the hydrophobic phase is discharged and a further substream of the hydrophobic phase is used as reflux in the thermal separation process. Particular preference is given to a reflux ratio between what is recycled and what is discharged of in the range from 4:1 to 8:1.

Both the thermal separation process and the distillative separation of water and solvent can be operated continuously or batchwise.

The process according to the invention is particularly advantageously usable in the direct preparation of anhydrous aromatics. For the purposes of the present disclosure, “anhydrous” means that the water content of the aromatics fraction after the extractive distillation immediately satisfies the requirements placed on the pure product and no drying steps downstream of the extractive distillation need to be carried out. In particular, it is then not necessary to remove a separate water phase from the condensed aromatics fraction. In such processes, the solvent in the solvent circuit (bottom of the stripper column) typically has a water content of less than 1% by mass, preferably less than 0.5% by mass and particularly preferably less than 1000 ppm. Moreover, no steam is added to the stripper column in this variant either, since this would result in an increased water content in the aromatics fraction.

Solvents useful for the extractive distillation include, inter alia, sulfolane, methylsulfolanes, N-methylpyrrolidone, N-formylmorpholine, ethylene glycol and mixtures thereof, and also mixtures of the mentioned solvents with water. Particularly preferably, the solvent contains N-formylmorpholine, which is particularly suitable for the direct preparation of anhydrous aromatics.

In terms of apparatus, the object is achieved by an apparatus for separating a hydrocarbon-containing feedstock stream by extractive distillation into at least one aliphatics product stream and one aromatics product stream, comprising:

- a device for contacting the feedstock stream with a water-soluble solvent for aromatics in countercurrent,
- a device for distillatively removing an aliphatics fraction from the mixture obtained to leave behind the aromatics-enriched solvent, with a discharge for the aliphatics fraction as aliphatics product stream,
- a device for stripping the aromatics from the aromatics-enriched solvent with a discharge for the aromatics as aromatics product stream,
- a recycle line for the aromatics-depleted solvent in a solvent circuit to the device for contacting the feedstock stream with solvent, and
- a purification device for the solvent, which is arranged in the solvent circuit and through which at least temporarily at least a substream of the aromatics-depleted solvent passes during operation, for the removal of impurities comprising compounds having a lower boiling point compared to the solvent from the substream.

According to the invention, the purification device comprises a thermal separation apparatus with a discharge for the thermal removal and discharge of the impurities in a top product of the thermal separation apparatus. The purification device further includes a recycle line for the purified solvent that remains into the solvent circuit.

In preferred embodiments, the discharge of the purification apparatus for the top product is connected to a solvent recovery device. Arranged in the solvent recovery device are at least one mixing apparatus for the addition of water to form an aqueous phase and a hydrophobic phase and at least one separating apparatus for separating the aqueous phase from the hydrophobic phase. The solvent recovery device further includes a discharge for the aqueous phase which is connected to a distillation column for the removal of the water by distillation. The distillation column includes a discharge for a bottom product of the distillation column, via which the bottom product is recyclable into the solvent circuit.

The distillation column preferably includes a top discharge for the water removed by distillation, which is connected to the mixing apparatus for the addition of water to form a water circuit.

Furthermore, arranged upstream of the purification apparatus is preferably at least one heat exchanger for cooling the substream, which is connected to the distillation column for transfer of the heat energy obtained in the heat exchanger.

In preferred embodiments, the distillation column is connected to a vacuum generation device configured to generate a negative pressure of less than 1 bar (a), preferably less than 500 mbar (a) and particularly preferably less than 200 mbar (a) in a top region of the distillation column.

In further preferred embodiments, a branch-off for a discharge of a substream of the hydrophobic phase is provided and a further substream of the hydrophobic phase is suppliable as reflux to the purification apparatus via a feed.

Furthermore, arranged between the thermal separation apparatus and the solvent recovery device is preferably a second heat exchanger for cooling the top product. The top product is particularly preferably obtained with a temperature of greater than 120° C., is cooled in a heat exchanger and enters the solvent recovery device with a temperature in the range from 0° C. to 60° C. Recovery at a lower temperature compared to the temperature of the thermal separation is preferred since this reduces the solubility of the impurities in the solvent. Excessively low temperatures should be avoided, in order to prevent solidification of the solvent.

Further advantageous embodiments can be gathered from the following description and the dependent claims.

In the various figures, identical parts are always provided with the same reference signs and are therefore also generally named or mentioned only once.

FIG. 1 shows a flow diagram of the process 100 according to the invention according to a first exemplary embodiment of the invention. In the process 100, a hydrocarbon-containing feedstock stream 1 is separated by extractive distillation into at least one aliphatics product stream 2 and one aromatics product stream 3.

Process 100 comprises the following steps:

In step 110, the feedstock stream 1 is contacted with a water-soluble solvent 4 for aromatics in countercurrent, and a mixture 5 is formed. Then, in step 120, an aliphatics fraction is distillatively removed from the mixture 5 obtained to leave behind the aromatics-enriched solvent 6 and the aliphatics fraction is discharged in the aliphatics product stream 2. Next, in step 130, the aromatics are stripped from the aromatics-enriched solvent 6 and the aromatics are discharged in the aromatics product stream 3. The stripping is preferably effected at a higher temperature and/or higher pressure compared to the distillative removal of the aliphatics fraction. The aromatics-depleted solvent 4 is recycled in step 140 in a solvent circuit 7 for the extraction of further aromatics from the feedstock stream 1.

When carrying out the process 100, compounds having a lower boiling point compared to the solvent 4 accumulate, inter alia, in the solvent circuit 7 as impurities. These impurities are at the same time high-boiling enough that they cannot leave the solvent circuit 7 via the distillative removal 120 or the stripping of the aromatics 130. Accordingly, in step 150 there is provided a purifying at least of a substream 8 of the aromatics-depleted solvent 4 for removal of the impurities. For the purifying 150, the substream 8 is subjected to a thermal separation process, in which the impurities are at least partly discharged in a top product 11 and the purified solvent 10 that remains is recycled into the solvent circuit 7.

There may be provision for the purifying 150 of the solvent 4 to be effected only temporarily during the implementation of the process. To this end, the substream 8 may for example be controllable via a control valve. The volume flow rate of the substream 8 is preferably regulated such that the impurities in the solvent are adjusted to a target value or target range. The target value or target range for the impurities in the solvent is preferably in the range from 0.1-20% by mass, preferably 0.1-10% by mass and particularly preferably 1-5% by mass. In this way, the consumption of operating materials required for ensuring exceptional selectivity and capacity of the solvent can be reduced.

The thermal separation process provided is preferably a distillation or rectification. The thermal separation process may be one-stage or multistage. For example, a one-stage or multistage distillation or a one-stage or multistage flash is conceivable.

In the exemplary embodiment according to FIG. 1, a recovery of solvent from the top product 11 of the thermal separation process is further provided. For this purpose, the following further steps are carried out:

In step 160, water 14 is added to the top product 11 of the thermal separation process to form an aqueous solvent-containing phase 12 and a hydrophobic phase 13. Preference is given to adding water to the top product in a ratio by mass in the range from 30:1 to 1:3, in particular 20:1 to 1:2 and particularly preferably 10:1 to 1:1. Then, in step 170, the aqueous phase 12 is separated from the hydrophobic phase 13. Finally, in step 180, provision is made for distillation of the aqueous phase 12 for the removal of the water by distillation, with the bottom product 15 of the distillation 180 being recycled into the solvent circuit 7.

The distillation 180 is preferably carried out with a top pressure of less than 1 bar (a), more preferably less than 500 mbar (a) and particularly preferably less than 200 mbar (a). The bottom temperatures of the distillation 180 are preferably set in the range of less than 230° C., preferably in the range 150-200° C.

It is further preferably provided that the water 14 removed by distillation is recycled in a water circuit 16 and again added to the top product 11 of the thermal separation process.

A substream 18 of the hydrophobic phase 13 can be discharged. For example, the substream 18 can, as shown in FIG. 1, be discharged to the plant limits as a separate stream. To the extent that the specifications of the aliphatics product stream 2 permit it, this substream 18 can also be admixed with the aliphatics product stream 2 (not shown). A further substream 9 of the hydrophobic phase is preferably used as reflux in the thermal separation process.

For the saving of energy it can preferably be provided that the substream 8 is cooled in a heat exchanger prior to carrying out the thermal separation process and the distillation is carried out using the heat energy obtained in the heat exchanger. Furthermore, the top product 11 is preferably cooled prior to recovering the solvent from the top product 11.

The solvent 4 in the solvent circuit 7 preferably has a water content of less than 3% by mass, more preferably less than 1% by mass and particularly preferably less than 1000 ppm.

In preferred process variants, the solvent 4, 6 contains N-formylmorpholine. Particularly preferably, the solvent 4 contains a proportion by mass of at least 50% N-formylmorpholine.

Figure 2:
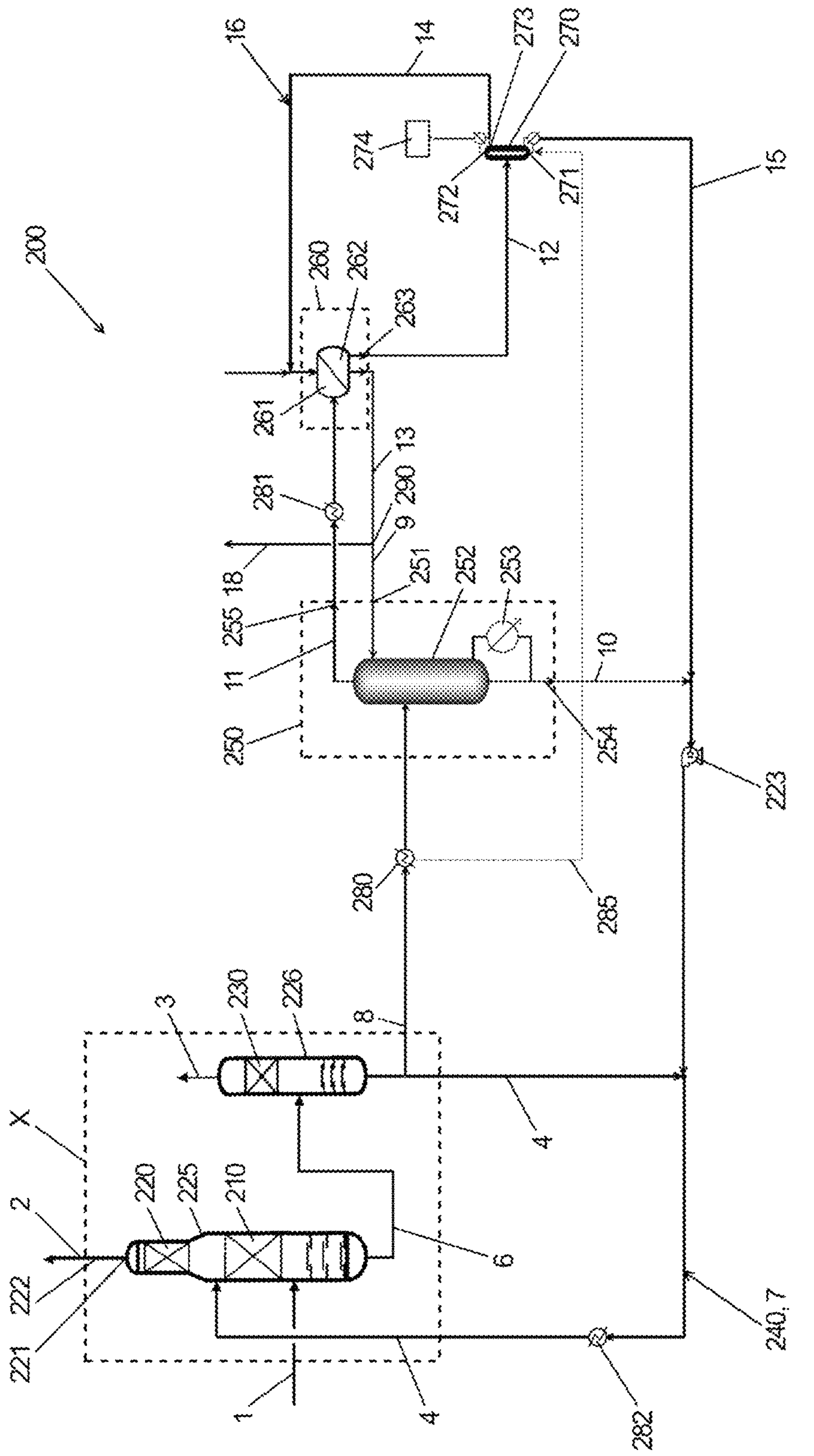
FIG. 2 schematically shows a first exemplary embodiment of the apparatus according to the invention, which is suitable for performing the process shown in FIG. 1.

FIG. 2 shows an exemplary embodiment of the apparatus 200 according to the invention for separating a hydrocarbon-containing feedstock stream 1 by extractive distillation into at least one aliphatics product stream 2 and one aromatics product stream 3. The apparatus comprises a device 210 for contacting the feedstock stream with a water-soluble solvent 4 for aromatics in countercurrent, a device for distillatively removing an aliphatics fraction 220 from the mixture 5 obtained to leave behind the aromatics-enriched solvent 6, with a discharge 221 for the aliphatics fraction as aliphatics product stream 2, and a device for stripping 230 the aromatics from the aromatics-enriched solvent 6 with a discharge for the aromatics as aromatics product stream.

The apparatus further comprises a recycle line 240 for the aromatics-depleted solvent 4 in a solvent circuit 7 to the device 210 for contacting the feedstock stream 1 with solvent 4 in countercurrent, and a purification device 250 for the solvent 4, which is arranged in the solvent circuit 7 and through which at least a substream 8 of the aromatics-depleted solvent 4 passes during operation, for the removal of impurities comprising compounds having a lower boiling point compared to the solvent from the substream 8.

The purification device 250 comprises a thermal separation apparatus 252 with a discharge 255 for the thermal removal and discharge of the impurities in a top product 11, and a recycle line 254 for the purified solvent 10 that remains into the solvent circuit 7. The purified solvent 10 can be supplied to the solvent circuit 7 for example via a pump 223.

The thermal separation apparatus 252 can, as illustrated in FIG. 2, be formed for example by a distillation column, which can preferably be equipped in the bottom region with a reboiler 253. Alternatively or in addition, multistage distillations and/or a one-stage or multistage flash are also usable as thermal separation apparatus 252.

The purification apparatus 250 further includes a discharge 255 for the top product 11 of the thermal separation process, which is connected to a solvent recovery device 260. Arranged in the solvent recovery device 260 are at least one mixing apparatus 261 for the addition of water 14 to form an aqueous phase 12 and a hydrophobic phase 13 and at least one separating apparatus 262 for separating the aqueous phase 12 from the hydrophobic phase 13.

The solvent recovery device 260 may be of one-stage or multistage design. The mixing apparatus 261 may be formed together with the separating apparatus 262 in one vessel, for example a mixer-settler unit or else as a one-stage or multistage extraction column. However, the mixing apparatus 261 can also be formed merely by a pipeline branch via which water can be fed into the stream of the top product 11.

Preferably, top product 11 and water 14 are conducted in countercurrent in the solvent recovery device 260. Particularly preferably, in multistage recovery devices 260, the addition of water 14 is effected by adding the aqueous phase 12 from the respective following stage. In this way, the solvent accumulates over the stages in the aqueous phase in the opposite direction to the concentration of the solvent in the hydrophobic phase 13. The use of fresh or treated water can be reduced as a result.

The solvent recovery device 260 includes a discharge 263 for the aqueous phase 12 which is connected to a distillation column 270 for the removal of the water 14 by distillation. The distillation column 270 has a discharge 271 for a bottom product 15 of the distillation column 270, via which the bottom product 15 is recyclable into the solvent circuit 7.

The distillation column 270 further includes a top discharge 272 for the water 14 removed by distillation, which is connected to the mixing apparatus 261 for the addition of water 14 to form a water circuit 16.

The distillation column 270 is preferably connected to a vacuum generation device 274 configured to generate a negative pressure of less than 1 bar (a), preferably less than 500 mbar (a) and particularly preferably less than 200 mbar (a) in a top region 273 of the distillation column 270.

Preference is given to providing heat integration of the distillation column 270. To this end, arranged upstream of the purification apparatus 250 can be at least one heat exchanger 280 for cooling the substream 8, which is connected to the distillation column 270 for transfer of the heat energy 285 obtained in the heat exchanger 280. Particularly preferably, the entire energy requirement of the distillation column 270 is covered by the heat energy 285 transferred.

Prior to entering the solvent recovery device 260, the top product 11 can be cooled in a second heat exchanger 281. The cooling in the heat exchanger 281 is preferably effected down to a temperature range from 0° C. to 60° C. The heat energy additionally obtained in this heat exchanger 281 can be used for example to heat the aqueous phase 12 prior to entering the distillation column 270.

After emerging from the solvent recovery device 260, the hydrophobic phase 13 can be provided a branch-off 290 for a discharge of a substream 18 of the hydrophobic phase 13. A further substream 9 of the hydrophobic phase 13 can be supplied as reflux to the purification apparatus 250 via a feed 251. The substream 18 can be discharged as a separate stream to the plant limits, or else for example be admixed with the aliphatics product stream 2.

In the exemplary embodiment illustrated in FIG. 2, the main process of the extractive distillation is illustrated in the section X. Here, the device for contacting in countercurrent 210 and the device for distillative removal 220 are combined in a column for extractive distillation 225 and a separate stripper column 226 is provided for the device for stripping 230.

Figure 3:
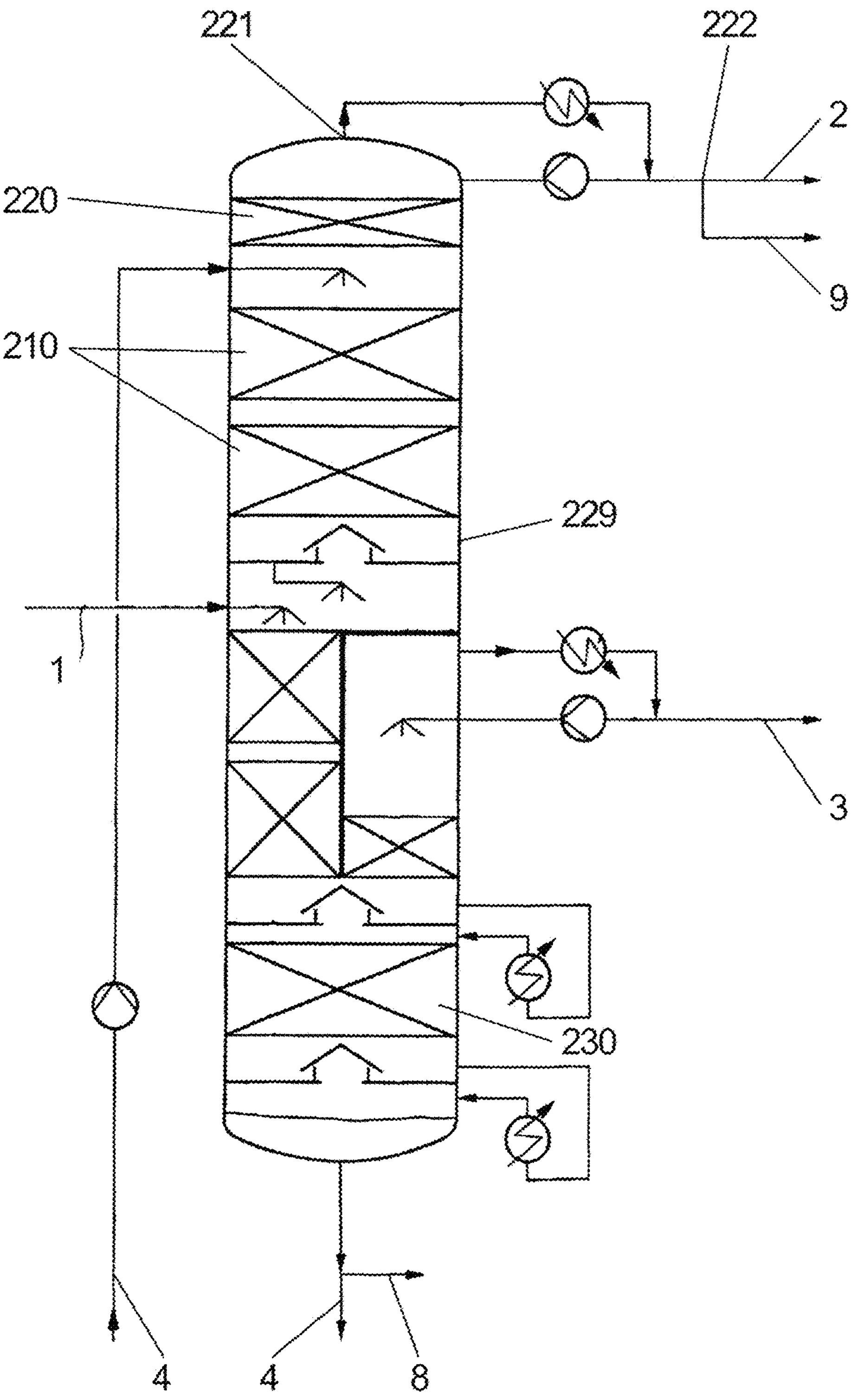
FIG. 3 schematically shows an alternative apparatus construction to the section X in FIG. 2, for carrying out the extractive distillation in a single column for extractive distillation.

FIG. 3 shows an alternative apparatus construction for the section X in the apparatus according to FIG. 2. In the construction illustrated in FIG. 3, the device for contacting in countercurrent 210, the device for distillative removal 220 and the device for stripping 230 are combined in a single column for extractive distillation 229 with integrated stripping. The advantages of this construction are for example a lower apparatus expenditure and a lower space requirement for the apparatus 200.

Figure 4:
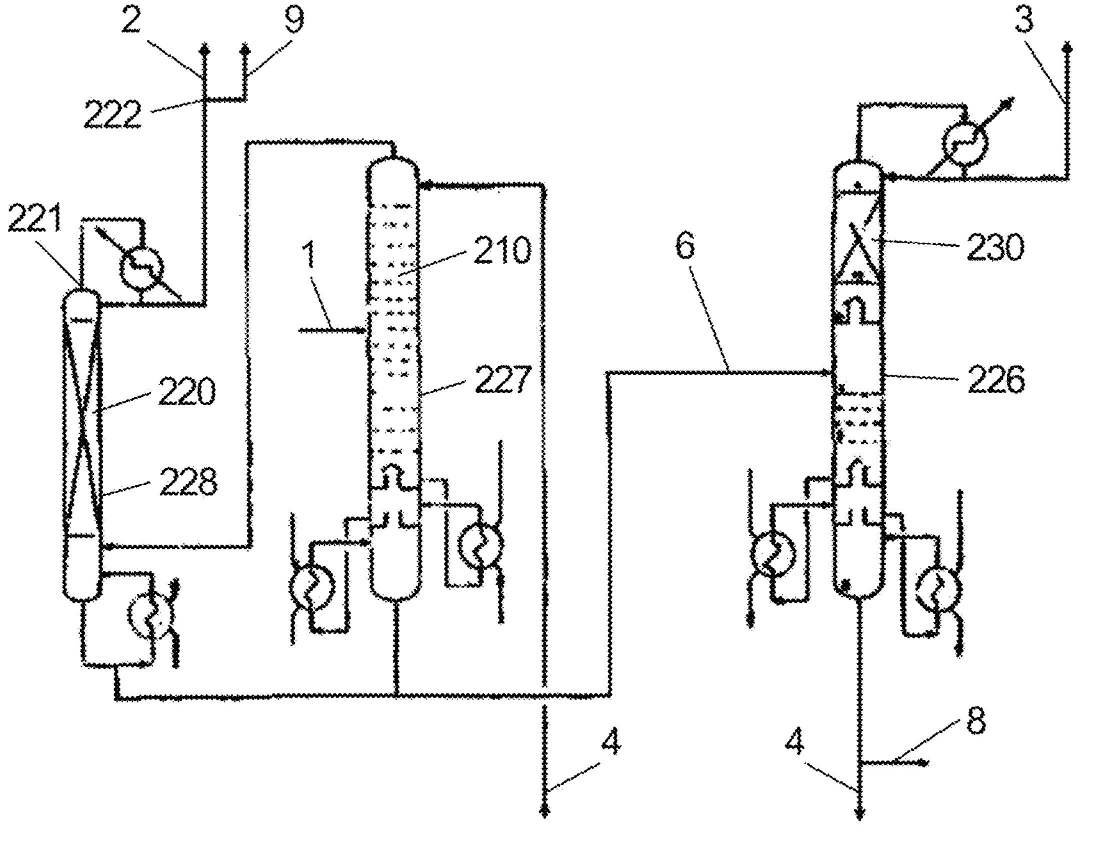
FIG. 4 schematically shows an alternative apparatus construction to the section X in FIG. 2, for carrying out the extractive distillation in three separate columns.

FIG. 4 shows a further alternative apparatus construction for the section X in the apparatus according to FIG. 2. In the construction illustrated in FIG. 4, a column for extractive distillation 227 is provided for the device for contacting in countercurrent 210 and a dedicated column for raffinate purification 228 is provided for the device for distillative removal 220. The device for stripping 230 is arranged in a separate stripper column 226. The advantages of this construction reside in the lower installation height for the column for extractive distillation 227. This construction can thus preferably be used in the case of practical or legal authorization restrictions in the installation height of the plant.

LIST OF REFERENCE SIGNS

1 Feedstock stream
2 Aliphatics product stream
3 Aromatics product stream
4 Solvent for aromatics
5 Mixture of feedstock and solvent
6 Aromatics-enriched solvent
7 Solvent circuit
8 Substream of the solvent circuit
9 Substream of the hydrophobic phase
10 Purified solvent
11 Top product of the thermal separation process
12 Aqueous phase
13 Hydrophobic phase
14 Water
15 Bottom product of the distillation
16 Water circuit
18 Substream of the hydrophobic phase
100 Process for separating a hydrocarbon-containing feedstock stream

110 Contacting of feedstock stream with solvent in countercurrent
120 Distillative removal of an aliphatics fraction
130 Stripping of the aromatics from the solvent
140 Recycling of the solvent
150 Purifying of the substream of the aromatics-depleted solvent
160 Adding of water
170 Separating of the aqueous phase from the hydrophobic phase
180 Distillation of the aqueous phase
200 Apparatus for separating a hydrocarbon-containing feedstock stream
210 Device for contacting in countercurrent
220 Device for distillative removal
221 Discharge
222 Branch-off
223 Pump
225, 227 Column for extractive distillation
226 Stripper column
228 Column for raffinate purification
229 Column for extractive distillation with integrated stripping
230 Device for stripping
240 Recycle line for the solvent
250 Purification device
251 Feed for the purification device
252 Thermal separation apparatus
253 Reboiler
254 Recycle line for purified solvent
255 Discharge for top product
260 Solvent recovery device
261 Mixing apparatus
262 Separating apparatus
263 Discharge for the aqueous phase
270 Distillation column
271 Discharge for the bottom product
272 Top discharge
273 Top region
274 Vacuum generation device
280 to 282 Heat exchanger
285 Heat energy
290 Branch-off

What is claimed is:

1. A process for separating a hydrocarbon-containing feedstock stream by extractive distillation into at least one aliphatics product stream and one aromatics product stream, comprising:

contacting the feedstock stream with a water-soluble solvent for aromatics in countercurrent to obtain a mixture;

in a first distillation separation process, distillatively removing an aliphatics fraction from the mixture obtained to leave behind an aromatics-enriched solvent and discharging the aliphatics fraction in the aliphatics product stream;

stripping the aromatics from the aromatics-enriched solvent and discharging the aromatics in the aromatics product stream to obtain an aromatics-depleted solvent;

recycling the aromatics-depleted solvent in a solvent circuit for extraction of further aromatics from the feedstock stream, with compounds having a lower boiling point compared to the solvent accumulating in the solvent circuit as impurities; and purifying at least a substream of the aromatics-depleted solvent for removal of the impurities, wherein the purifying includes subjecting the substream to a second distillation separation process or a rectification separation process, in which the impurities are at least partly discharged in a top product and purified solvent is recycled into the solvent circuit;

wherein, for recovery of solvent from the top product of the second distillation separation process or the rectification separation process, the process further comprises:

adding water to the top product of the second distillation separation process or rectification separation process to form an aqueous solvent-containing phase and a hydrophobic phase;

separating the aqueous phase from the hydrophobic phase; and in a third distillation separation process, distilling the aqueous phase for removal of water by distillation, with a bottom product of the distillation being recycled into the solvent circuit.

2. The process as claimed in claim 1, wherein water removed by distillation in the third distillation separation process is recycled in a water circuit and again added to the top product of the second distillation separation process or the rectification separation process.

3. The process as claimed in claim 2, wherein the substream is cooled in a heat exchanger prior to carrying out the second distillation separation process or the rectification separation process and the third distillation separation process is carried out using the heat energy obtained in the heat exchanger.

4. The process as claimed in claim 1, wherein the third distillation separation process is carried out with a top pressure of less than 200 mbar (a).

5. The process as claimed in claim 1, wherein a substream of the hydrophobic phase is discharged and a further substream of the hydrophobic phase is used as reflux in the second distillation separation process or the rectification separation process.

6. The process as claimed in claim 1, wherein the solvent in the solvent circuit has a water content of less than 1000 ppm.

7. The process as claimed in claim 1, wherein the solvent contains N-formylmorpholine.

8. The process as claimed in claim 1, wherein a temperature of the substream is in the range from 140° C. to 200° C.

9. An apparatus for separating a hydrocarbon-containing feedstock stream by extractive distillation into at least one aliphatics product stream and one aromatics product stream, comprising:

a device for contacting in countercurrent the feedstock stream with a water-soluble solvent for aromatics;

a first distillation separation device for distillatively removing an aliphatics fraction from a mixture obtained to leave behind an aromatics-enriched solvent, with a discharge for the aliphatics fraction as aliphatics product stream;

a device for stripping aromatics from the aromatics-enriched solvent with a discharge for the aromatics as aromatics product stream;

a recycle line for an aromatics-depleted solvent in a solvent circuit to the device for contacting in countercurrent the feedstock stream with solvent; and a purification device for the solvent, which is arranged in the solvent circuit and through which at least temporarily at least a substream of the aromatics-depleted solvent passes during operation, for removal of impurities comprising compounds having a lower boiling point compared to the solvent from the substream, wherein the purification device comprises a second distillation separation device or a rectification separation apparatus with a discharge for thermal removal and discharge of the impurities in a top product, and the purification device includes a recycle line for purified solvent that remains into the solvent circuit;

wherein the discharge for the top product of the second distillation separation device or the rectification separation apparatus is connected to a solvent recovery device in which at least one mixing apparatus for addition of water to form an aqueous phase and a hydrophobic phase and at least one separating apparatus for separating the aqueous phase from the hydrophobic phase are arranged, wherein the solvent recovery device includes a discharge for the aqueous phase which is connected to a third distillation separation device including a distillation column for removal of the water by distillation and the distillation column includes a discharge for a bottom product of the distillation column, via which the bottom product is recyclable into the solvent circuit.

10. The apparatus as claimed in claim 9, wherein the distillation column includes a top discharge for the water removed by distillation, which is connected to the mixing apparatus for the addition of water to form a water circuit.

11. The apparatus as claimed in claim 9, wherein arranged upstream of the purification apparatus is at least a first heat exchanger for cooling the substream, which is connected to the distillation column for transfer of the heat energy obtained in the first heat exchanger.

12. The apparatus as claimed in claim 9, wherein the distillation column is connected to a vacuum generation device configured to generate a negative pressure of less than 200 mbar (a) in a top region of the distillation column.

13. The apparatus as claimed in claim 9, wherein a branch-off for a discharge of a substream of the hydrophobic phase is provided and a further substream of the hydrophobic phase is suppliable as reflux to the purification apparatus via a feed.

14. The apparatus as claimed in claim 9, wherein arranged between the second distillation separation device or the rectification separation apparatus and the solvent recovery device is a second heat exchanger for cooling the top product.

15. The apparatus as claimed in claim 9, wherein a temperature of the substream is in the range from 140° C. to 200° C.

* * * * *